United States Patent
Keshwani et al.

(10) Patent No.: US 11,983,879 B2
(45) Date of Patent: May 14, 2024

(54) IMAGE PROCESSING APPARATUS, IMAGE PROCESSING METHOD, AND PROGRAM

(71) Applicant: FUJIFILM Corporation, Tokyo (JP)

(72) Inventors: Deepak Keshwani, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 403 days.

(21) Appl. No.: 17/326,340

(22) Filed: May 21, 2021

(65) Prior Publication Data

US 2021/0272290 A1 Sep. 2, 2021

Related U.S. Application Data

(63) Continuation of application No. PCT/JP2019/044868, filed on Nov. 15, 2019.

(30) Foreign Application Priority Data

Nov. 30, 2018 (JP) ................................. 2018-225020

(51) Int. Cl.
*G06T 7/11* (2017.01)
*G06N 3/04* (2023.01)
(Continued)

(52) U.S. Cl.
CPC ................ *G06T 7/11* (2017.01); *G06N 3/04* (2013.01); *G06T 5/20* (2013.01); *G06T 5/92* (2024.01);
(Continued)

(58) Field of Classification Search
CPC ... G06T 7/11; G06T 5/009; G06T 5/20; G06T 2207/20081; G06T 2207/20084;
(Continued)

(56) References Cited

U.S. PATENT DOCUMENTS 7,738,683 B2  6/2010  Cahill et al.
9,589,374 B1 * 3/2017  Gao ..................... A61B 6/5211
(Continued)

FOREIGN PATENT DOCUMENTS

JP  2009502230  1/2009
JP  2014502169  1/2014
(Continued)

OTHER PUBLICATIONS

Satoshi et al. "Let there be color! Joint end-to-end learning of global and local image priors for automatic image colorization with simultaneous classification," (Year: 2016).*
(Continued)

*Primary Examiner* — Stephen P Coleman
(74) *Attorney, Agent, or Firm* — JCIPRNET

(57) ABSTRACT

Provided are an image processing apparatus, an image processing method, and a program that can suppress an error in the segmentation of a medical image. An image processing apparatus includes: a segmentation unit (42) that applies deep learning to perform segmentation which classifies a medical image (200) into a specific class on the basis of a local feature of the medical image; and a global feature classification unit (46) that applies deep learning to classify the medical image into a global feature which is an overall feature of the medical image. The segmentation unit shares a weight of a first low-order layer which is a low-order layer with a second low-order layer which is a low-order layer in the global feature classification unit.

12 Claims, 9 Drawing Sheets

(51) Int. Cl.
  *G06T 5/20* (2006.01)
  *G06T 5/92* (2024.01)
  *G06V 10/764* (2022.01)
  *G16H 30/40* (2018.01)

(52) U.S. Cl.
  CPC .......... *G06V 10/764* (2022.01); *G16H 30/40* (2018.01); *G06T 2207/20081* (2013.01); *G06T 2207/20084* (2013.01); *G06T 2207/30096* (2013.01)

(58) Field of Classification Search
  CPC ........ G06T 2207/30096; G06T 7/0012; G06N 3/04; G06N 3/045; G06V 10/764; G06V 2201/03; G16H 30/40; G16H 50/20; A61B 6/00; A61B 6/03
  USPC ......................................................... 382/173
  See application file for complete search history.

(56) References Cited

U.S. PATENT DOCUMENTS

| | | | |
|---|---|---|---|
| 10,387,773 | B2 | 8/2019 | Yan et al. |
| 2013/0208964 | A1 | 8/2013 | Dwivedi |
| 2016/0048741 | A1* | 2/2016 | Nguyen ................ G06F 18/214 382/155 |
| 2017/0161894 | A1* | 6/2017 | Fisher ....................... G06T 7/11 |
| 2018/0260687 | A1 | 9/2018 | Kanno et al. |
| 2018/0293465 | A1 | 10/2018 | Kanada |
| 2019/0340197 | A1* | 11/2019 | Sugaya ................ G06V 10/774 |

FOREIGN PATENT DOCUMENTS

| | | |
|---|---|---|
| JP | 2017538195 | 12/2017 |
| JP | 2018175226 | 11/2018 |
| WO | 2017187516 | 11/2017 |

OTHER PUBLICATIONS

Satoshi Iizuka et al., "Let there be Color!: Joint End-to-end Learning of Global and Local Image Priors for Automatic Image Colorization with Simultaneous Classification", ACM Transactions on Graphics, Jul. 11, 2016, pp. 1-11.

Xiaosong Wang et al., "ChestX-Ray8: Hospital-Scale Chest X-Ray Database and Benchmarks on Weakly-Supervised Classification and Localization of Common Thorax Diseases", 2017 IEEE Conference on Computer Vision and Pattern Recognition (CVPR), Dec. 14, 2017, pp. 1-18.

Jingjing Zhuge et al., "Automatic colorization using fully convolutional networks", Journal of Electronic Imaging, Jul. 27, 2018, pp. 1-13.

"International Search Report (Form PCT/ISA/210) of PCT/JP2019/044868," dated Jan. 28, 2020, with English translation thereof, pp. 1-7.

"Written Opinion of the International Searching Authority (Form PCT/ISA/237) of PCT/ JP2019/044868," dated Jan. 28, 2020, with English translation thereof, pp. 1-13.

"Office Action of Japan Counterpart Application" with English translation thereof, dated Apr. 6, 2022, p. 1-p. 10.

* cited by examiner

| DISEASE NAME (GLOBAL FEATURE) | LESION (CLASS) THAT CAN EXIST |
|---|---|
| COLLAGEN DISEASE LUNG ① RA | tree-in-bud appearance, BRONCHIECTASIS, TRACTION BRONCHIECTASIS, GROUND-GLASS OPACITY, HONEYCOMB LUNG |
| COLLAGEN DISEASE LUNG ② SSc (PSS) | BRONCHIECTASIS, TRACTION BRONCHIECTASIS, GROUND-GLASS OPACITY |
| CRYPTOGENIC ORGANIZING PNEUMONIA COP/OP | CONSOLIDATION, AIR BRONCHOGRAM, TRACTION BRONCHIECTASIS, GROUND-GLASS OPACITY |
| CRYPTOGENIC ORGANIZING PNEUMONIA UPPER LOBE PREDOMINANT PULMONARY FIBROSIS (PLEUROPARENCHYMAL FIBROELASTOSIS) | CONSOLIDATION, AIR BRONCHOGRAM, TRACTION BRONCHIECTASIS, GROUND-GLASS OPACITY, INTERLOBULAR SEPTAL THICKENING |
| SARCOIDOSIS: ONLY LUNG FIELD LESION | NODULAR SHADOW, GROUND-GLASS OPACITY, INTERLOBULAR SEPTAL THICKENING, BRONCHOVASCULAR BUNDLE |
| unclassifiable INTERSTITIAL PNEUMONIA | TRACTION BRONCHIECTASIS, GROUND-GLASS OPACITY, INTERLOBULAR SEPTAL THICKENING, HONEYCOMB LUNG |
| IPF ACUTE EXACERBATION | TRACTION BRONCHIECTASIS, GROUND-GLASS OPACITY, INTERLOBULAR SEPTAL THICKENING, HONEYCOMB LUNG |
| HYPERSENSITIVITY PNEUMONITIS ① SUMMER TYPE | GROUND-GLASS OPACITY, CENTRILOBULAR, MAP-LIKE |
| HYPERSENSITIVITY PNEUMONITIS ② BIRD-RELATED (INCLUDING CHRONIC TYPE) | GROUND-GLASS OPACITY, CENTRILOBULAR, MAP-LIKE |
| DIP/DIP | GROUND-GLASS OPACITY |
| CHRONIC NECROTIZING PULMONARY ASPERGILLOSIS (CNPA) | CONSOLIDATION, CAVITY, AIR BRONCHOGRAM, BRONCHIECTASIS |
| NON-TUBERCULOUS MYCOBACTERIOSIS ② *M. intracellulare* | CONSOLIDATION, CAVITY, BRONCHIAL WALL THICKENING, BRONCHIECTASIS |
| PSEUDOMONAS PNEUMONIA | CONSOLIDATION, CAVITY, BRONCHIECTASIS, tree-in-bud appearance |
| PULMONARY MUCORMYCOSIS | CONSOLIDATION, CAVITY, BRONCHIECTASIS |
| IPF/UIP | TRACTION BRONCHIECTASIS, GROUND-GLASS OPACITY, INTERLOBULAR SEPTAL THICKENING, HONEYCOMB LUNG |

IMAGE PROCESSING APPARATUS, IMAGE PROCESSING METHOD, AND PROGRAM

CROSS-REFERENCE TO RELATED APPLICATIONS

The present application is a Continuation of PCT International Application No. PCT/JP2019/044868 filed on Nov. 15, 2019 claiming priority under 35 U.S.C § 119(a) to Japanese Patent Application No. 2018-225020 filed on Nov. 30, 2018. Each of the above applications is hereby expressly incorporated by reference, in its entirety, into the present application.

BACKGROUND OF THE INVENTION

1. Field of the Invention

The present invention relates to an image processing apparatus, an image processing method, and a program, and more particularly, to segmentation of a medical image.

2. Description of the Related Art

The segmentation of a medical image based on anatomical features using deep learning is known. In the segmentation of the medical image, for example, a pixel is classified into a specific class on the basis of the features of a local region around the pixel or a voxel.

JP2009-502230A discloses a system that detects an injured part from a medical image of a subject. The system disclosed in JP2009-502230A designates the features of the injured part in two types of medical images generated by different methods and detects, for example, a region corresponding to the designated features as the injured part.

JP2014-502169A discloses a system that acquires a medical image, acquires the image features of the medical image, categorizes the medical image depending on the image features, selects a segmentation algorithm depending on the category, and segments the medical image using the selected segmentation algorithm.

JP2017-538195A discloses a convolutional neural network (CNN) for image classification. The CNN disclosed in JP2017-538195A comprises a classification module that receives image data, determines a rough category of an image or a weight for the rough category using a rough category CNN, and determines a precise category of the image using one or more precise category CNNs.

WO2017/187516A discloses a system in which a machine learning recognition device in a first layer and a machine learning recognition device in a second layer are hierarchically connected. The machine learning recognition device in the second layer disclosed in WO2017/187516A uses data of an interlayer in the machine learning recognition device in the first layer as an input.

SUMMARY OF THE INVENTION

However, in the segmentation of the medical image, an error is likely to occur in the classified class. For example, in a case in which segmentation is performed on the basis of information of a local region, there is a concern that an inaccurate segmentation result with a large amount of noise will be generated.

Specifically, a GGO pattern of the lung is defined as a region having a higher CT value than the normal lung. On the other hand, since an IPF patient is not able to breathe sufficiently, the CT value of the lung of the IPF patient is high. In a case in which segmentation is performed on the basis of the information of only a local region, a normal lung region is likely to be recognized as the GGC pattern.

That is, it is difficult to determine whether a region of the lung is a normal lung region or a GGO region using only the CT value. In addition, GGO is an abbreviation of Ground Glass Opacity. CT is an abbreviation of Computed Tomography.

The system disclosed in JP2009-502230A detects a specific injured part from a medical image. That is, JP2009-502230A discloses classification that specifies an injury name of a medical image from the overall features of the medical image, but does not disclose segmentation that classifies each pixel of a medical image into a specific class.

The system disclosed in JP2014-502169A selects a segmentation algorithm on the basis of the features of a medical image in a case in which segmentation is performed on the medical image. However, in a case in which the segmentation algorithm performs segmentation on the basis of the features of a local region, such as a pixel, an error may occur in the result of the segmentation.

JP2017-538195A does not disclose the processing of a medical image and does not disclose segmentation that classifies each pixel of an image into a specific class. This holds for WO2017/187516A.

The invention has been made in view of the above-mentioned problems, and an object of the invention is to provide an image processing apparatus, an image processing method, and a program that can suppress an error in the segmentation of a medical image.

In order to achieve the object, the invention provides the following aspects.

According to a first aspect, there is provided an image processing apparatus comprising: a segmentation unit that applies deep learning to perform segmentation which classifies a medical image into a specific class on the basis of a local feature of the medical image; and a global feature classification unit that applies deep learning to classify the medical image into a global feature which is an overall feature of the medical image. The segmentation unit shares a weight of a first low-order layer which is a low-order layer with a second low-order layer which is a low-order layer in the global feature classification unit.

According to the first aspect, the segmentation of the medical image is performed by the segmentation unit having the low-order layer that shares the weight with the low-order layer of the global feature classification unit. Therefore, segmentation in which the global feature is reflected is performed, and it is possible to suppress an error in class classification in the segmentation of the medical image.

Preferably, the image processing apparatus comprises a medical image acquisition unit that acquires a medical image. Preferably, the image processing apparatus comprises a medical image storage unit that stores the acquired medical image.

The segmentation unit may extract the features of a local region from the medical image and generate a feature amount map classified for each local feature.

The local region or the local portion may include an aspect composed of one pixel. Each local region or each local portion may include the concept of each pixel.

One or more layers including a layer subsequent to an input layer among the interlayers of the segmentation unit may be applied as the first low-order layer. Among the interlayers of the global feature classification unit, a layer that extracts the same features as the first low-order layer of the segmentation unit in a case in which features are extracted from the medical image may be applied as the second low-order layer.

According to a second aspect, in the image processing apparatus according to the first aspect, the segmentation unit may apply a lesion as the class.

According to the second aspect, it is possible to perform segmentation that extracts a lesion in a medical image.

An image pattern having features that can be distinguished from normal human body tissues may be applied as the lesion.

According to a third aspect, in the image processing apparatus according to the first aspect or the second aspect, the global feature classification unit may apply a disease name as the global feature.

According to the third aspect, segmentation in which the disease name corresponding to the medical image is reflected is performed.

According to a fourth aspect, in the image processing apparatus according to any one of the first to third aspects, the global feature classification unit may apply an imaging condition of the medical image as the global feature.

According to the fourth aspect, segmentation in which the imaging condition corresponding to the medical image is reflected is performed.

The global feature classification unit may apply a plurality of different types of global features to one medical image.

According to a fifth aspect, in the image processing apparatus according to any one of the first to fourth aspects, the segmentation unit may include a first encoder unit that compresses features of the medical image and a decoder unit that decompresses the features of the medical image compressed by the first encoder unit. The global feature classification unit may include a second encoder unit that compresses the features of the medical image. The segmentation unit may share a weight that is applied to the first encoder unit as the weight of the first low-order layer with a weight applied to the second encoder unit.

According to the fifth aspect, the segmentation unit can extract the features of the medical image in which unnecessary dimensions including, for example, noise have been reduced.

According to a sixth aspect, the image processing apparatus according to the fifth aspect may further comprise: a conversion unit that expands an output image of the second encoder unit, which has been more compressed than an output image of the first encoder unit, in accordance with the output image of the first encoder unit; and a combination unit that combines the output image of the first encoder unit and the output image of the conversion unit.

According to the sixth aspect, the output image of the second encoder unit is expanded in accordance with the output image of the first encoder unit. Therefore, it is possible to combine the output image of the first encoder unit and the output image of the second encoder unit.

According to a seventh aspect, in the image processing apparatus according to the sixth aspect, the second encoder unit may transmit, to the conversion unit, an output image of an interlayer that is provided in a stage before an output unit outputting a one-dimensional feature vector and does not share weights with the first encoder unit.

According to the seventh aspect, the amount of information of the output image of the interlayer in the stage before the output unit is not reduced with respect to the one-dimensional feature vector output from the output unit of the second encoder unit. Therefore, it is possible to expand the output image whose amount of information is kept constant and to combine the output image with the output image of the first encoder unit.

According to an eighth aspect, in the image processing apparatus according to the sixth aspect or the seventh aspect, a deep learning device that has performed learning using an input image of the conversion unit and an output image of the combination unit as a learning set may applied as the conversion unit.

According to the eighth aspect, it is possible to improve the accuracy of the processing of the conversion unit and the combination unit.

According to a ninth aspect, in the image processing apparatus according to any one of the first to eighth aspects, a deep learning device which has performed learning for a layer that shares weights with the global feature classification unit, using a segmentation result of the segmentation unit, a classification result of the global feature classification unit, and the medical image input to the segmentation unit as a learning set, may be applied as the segmentation unit.

According to the ninth aspect, it is possible to achieve the segmentation unit whose robustness is improved with reference to the global feature.

According to a tenth aspect, in the image processing apparatus according to the ninth aspect, a deep learning device which has performed relearning for a layer that does not share weights with the global feature classification unit, using the medical image and the segmentation result after application of the segmentation unit as a learning set, may be applied as the segmentation unit.

According to the tenth aspect, it is possible to perform the efficient relearning of the segmentation unit.

According to an eleventh aspect, in the image processing apparatus according to any one of the first to eighth aspects, a deep learning device which has performed learning for a layer that shares weights with the segmentation unit, using an input image of the global feature classification unit and a classification result of the global feature classification unit as a learning set, may be applied as the global feature classification unit.

According to the eleventh aspect, it is possible to perform efficient learning in which the amount of information of the learning set is suppressed.

According to a twelfth aspect, there is provided an image processing method comprising: a segmentation step of applying deep learning to perform segmentation which classifies a medical image into a specific class on the basis of a local feature of the medical image; and a global feature classification step of applying deep learning to classify the medical image into a global feature which is an overall feature of the medical image. In the segmentation step, a weight of a first low-order layer which is a low-order layer in a segmentation unit is shared with a second low-order layer which is a low-order layer in a global feature classification unit.

According to the twelfth aspect, it is possible to obtain the same effect as that in the first aspect.

In the twelfth aspect, the same matters as those specified in the second to eleventh aspects can be appropriately combined with each other. In this case, the components that are in charge of the processes or functions specified in the image processing apparatus can be understood as components of the image processing method which are in charge of processes or functions corresponding to the processes or functions.

According to a thirteenth aspect, there is provided a program that causes a computer to implement: a segmentation function of applying deep learning to perform segmentation which classifies a medical image into a specific class on the basis of a local feature of the medical image; and a global feature classification function of applying deep learning to classify the medical image into a global feature which is an overall feature of the medical image. The segmentation function shares a weight of a first low-order layer which is a low-order layer in a segmentation unit with a second low-order layer which is a low-order layer in a global feature classification unit.

According to the thirteenth aspect, it is possible to obtain the same effect as that in the first aspect.

In the thirteenth aspect, the same matters as those specified in the second to eleventh aspects can be appropriately combined with each other. In this case, the components that are in charge of the processes or functions specified in the image processing apparatus can be understood as components of the program which are in charge of processes or functions corresponding to the processes or functions.

According to the invention, the segmentation of a medical image is performed using the segmentation unit having the low-order layer that shares weights with the low-order layer of the global feature classification unit. Therefore, segmentation in which the global feature is reflected is performed, and it is possible to suppress an error in class classification in the segmentation of the medical image.

BRIEF DESCRIPTION OF THE DRAWINGS

FIG. 9 is a diagram illustrating an example of a table indicating a correspondence relationship between a disease name and a lesion.

DESCRIPTION OF THE PREFERRED EMBODIMENTS

Figure 1:
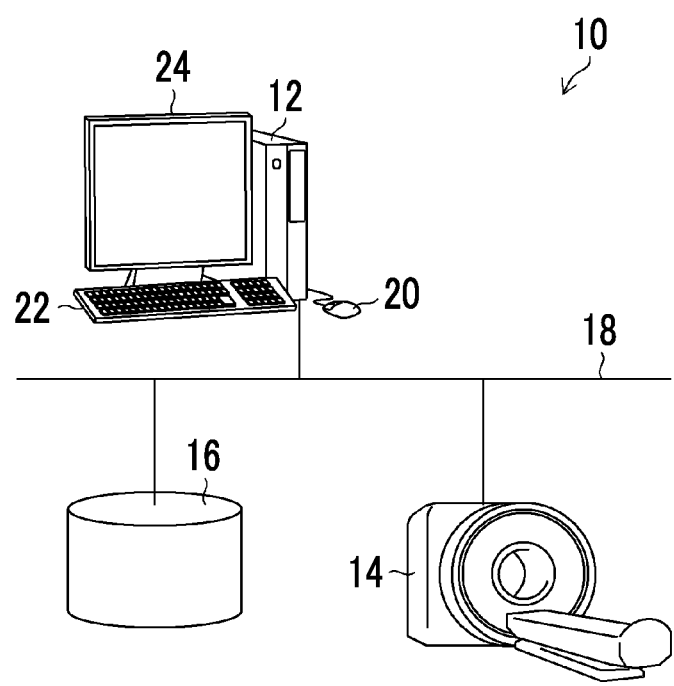
FIG. 1 is a diagram illustrating a schematic configuration of a medical information system according to an embodiment.

Hereinafter, preferred embodiments of the invention will be described in detail with reference to the accompanying drawings. In the specification, the same components are denoted by the same reference numerals and the duplicate description thereof will be appropriately omitted.

[Overall Configuration of Medical Image Processing System]

FIG. 1 is a diagram illustrating a schematic configuration of a medical information system according to an embodiment. A medical information system 10 comprises an image processing apparatus 12, a modality 14, and an image database 16. The image processing apparatus 12, the modality 14, and the image database 16 are connected through a network 18 so as to communicate with each other.

A computer provided in a medical institution can be applied as the image processing apparatus 12. A mouse 20 and a keyboard 22 as an input device are connected to the image processing apparatus 12. In addition, a display device 24 is connected to the image processing apparatus 12.

The modality 14 is an imaging apparatus that captures an image of an examination target part of a subject and generates a medical image. Examples of the modality 14 include an X-ray imaging apparatus, a CT apparatus, an MRI apparatus, a PET apparatus, an ultrasound apparatus, and a CR apparatus using a flat X-ray detector. An endoscopic apparatus may be applied as the modality 14.

In addition, MRI is an abbreviation of Magnetic Resonance Imaging. PET is an abbreviation of Positron Emission Tomography. In some cases, the flat X-ray detector is called a flat panel detector (FPD). CR is an abbreviation of Computed Radiography.

A DICOM standard can be applied as the format of the medical image. Accessory information defined by the DICOM standard may be added to the medical image. In addition, DICOM is an abbreviation of Digital Imaging and Communications in Medicine.

Here, the term "image" in the specification may include the meaning of image data which is a signal indicating an image in addition to the meaning of the image such as a photograph.

A computer comprising a high-capacity storage device can be applied as the image database 16. Software for providing the functions of a database management system is incorporated into the computer. In some cases, the database management system is called a database management system (DBMS).

A local area network (LAN) can be applied as the network 18. In addition, a wide area network (WAN) may be applied as the network 18. The DICOM standard can be applied as the communication protocol of the network 18. In addition, the network 18 may be configured so as to be connected to a public line network or may be configured so as to be connected to a leased line network. The network 18 may be a wired network or a wireless network.

[Image Processing Apparatus]
[Functions of Image Processing Apparatus]

Figure 2:
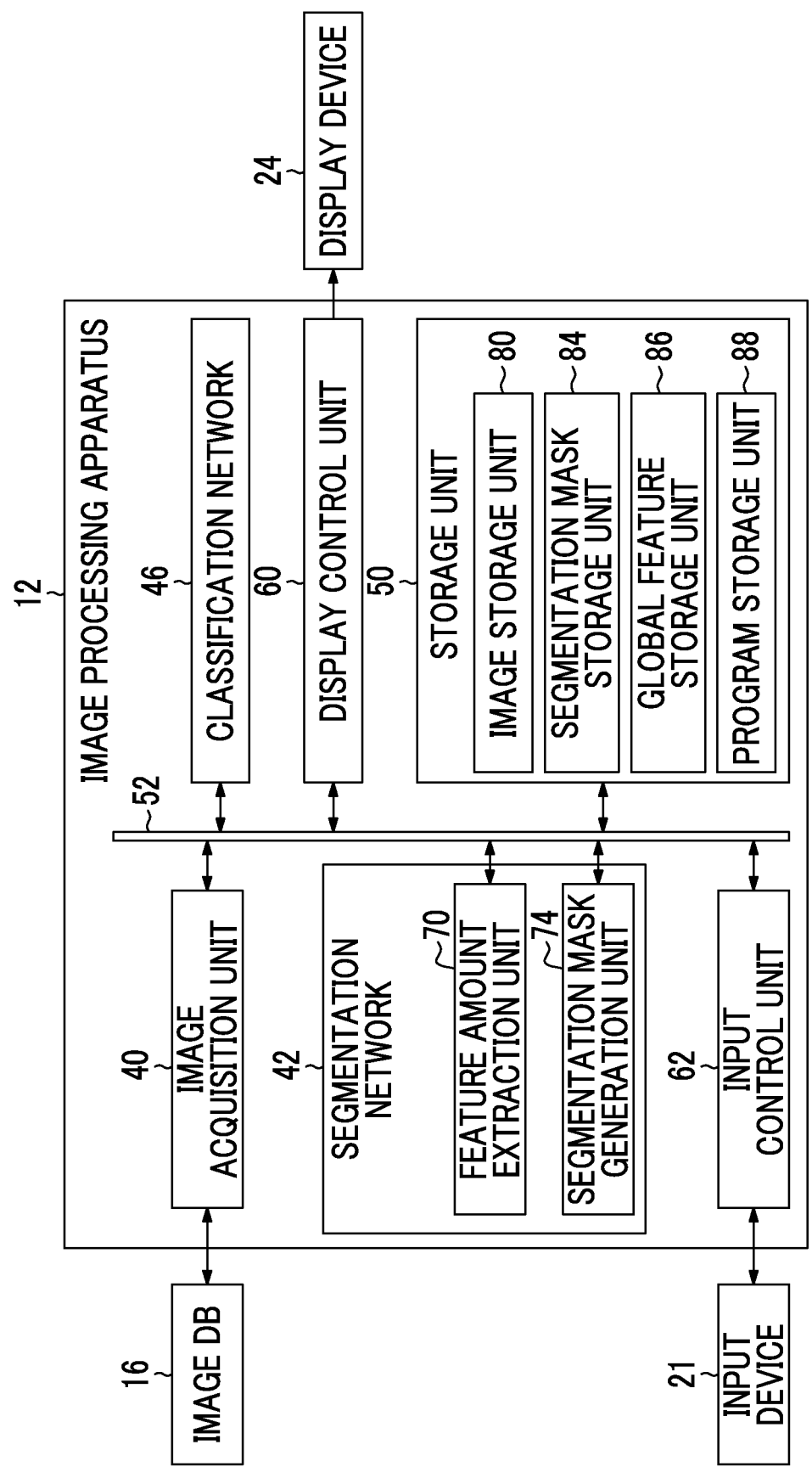
FIG. 2 is a functional block diagram illustrating an image processing apparatus illustrated in FIG. 1.

FIG. 2 is a functional block diagram illustrating the image processing apparatus illustrated in FIG. 1. The image processing apparatus 12 illustrated in FIG. 2 applies, for example, deep learning to generate a segmentation mask for a medical image. An example of the segmentation of the medical image is the classification of lung tissues into lesions which are tissues distinguishable from normal tissues, such as bronchiectasis, a honeycomb lung, ground-glass opacity, a reticular lung, and a linear lung.

For example, the segmented medical image is used to calculate the volume of each lesion. A change in the volume of each lesion is an index of the progression of a lung disease such as an interstitial lung disease.

In this embodiment, as the image processing apparatus 12, a discrimination apparatus will be described which automatically classifies whether or not each pixel in a CT image of the lung belongs to a class which is a medically known image pattern in a case in which the CT image of the lung is input. An example of the medically known image pattern is the above-described lesion.

The image processing apparatus 12 comprises an image acquisition unit 40, a segmentation network 42, and a classification network 46. The image processing apparatus 12 comprises a storage unit 50, a display control unit 60, and an input control unit 62.

The image acquisition unit 40, the segmentation network 42, the classification network 46, the storage unit 50, the display control unit 60, and the input control unit 62 are connected through a bus 52 so as to communicate with each other. Hereinafter, each unit of the image processing apparatus 12 will be described in detail.

The image acquisition unit 40 acquires the medical image to be processed. The image processing apparatus 12 stores the acquired medical image in the storage unit 50. FIG. 2 illustrates an aspect in which a medical image is acquired from the image database 16.

The image acquisition unit 40 may acquire a medical image from the modality 14 illustrated in FIG. 1 or may acquire a medical image from a storage device (not illustrated) through the network 18. In addition, the image acquisition unit 40 may acquire a medical image through an information storage medium.

The segmentation network 42 comprises a feature amount extraction unit 70 and a segmentation mask generation unit 74. The segmentation network 42 is a neural network that performs segmentation on the medical image acquired by the image acquisition unit 40. The segmentation network 42 according to the embodiment is an example of a segmentation unit.

That is, the segmentation network 42 extracts the feature amount of each pixel in the medical image, classifies each pixel on the basis of a local feature which is the feature amount of each pixel, and generates a segmentation mask for the medical image. The segmentation mask is denoted by reference numeral 210 in FIG. 4.

In addition, a plurality of consecutive pixels constitute a local region of the medical image. That is, the segmentation network 42 can perform classification for each local region on the basis of the local feature of each local region of the medical image. Hereinafter, processing for each pixel can be read as processing for each local region.

In this embodiment, a lesion is given as an example of the local feature. In the specification, the lesion may be called a lesion pattern, a finding, and the like.

The classification network 46 is a neural network that applies a global feature indicating the overall feature of the medical image to classify the medical image. The classification network 46 according to the embodiment is an example of a global feature classification unit.

Information input by an input device 21 or accessory information of the medical image may be applied as the global feature of the medical image. In this embodiment, examples of the global feature include a disease name and the imaging conditions of the medical image. The number of types of the global features is not limited as long as the number of global features is one or more.

The storage unit 50 stores various types of data in the image processing apparatus 12. The storage unit 50 comprises an image storage unit 80, a segmentation mask storage unit 84, a global feature storage unit 86, and a program storage unit 88. A plurality of storage devices or one storage device which is partitioned into a plurality of storage regions may be applied as the storage unit 50. One or more storage devices which are provided outside the image processing apparatus 12 may be applied as the storage unit 50.

The image storage unit 80 stores the medical image acquired by the image acquisition unit 40. The segmentation mask storage unit 84 stores the segmentation mask generated as the result of the segmentation. The global feature storage unit 86 stores the global feature of each medical image classified by the classification network 46.

The program storage unit 88 stores various programs executed in the image processing apparatus 12. The image processing apparatus 12 executes various programs using the hardware illustrated in FIG. 3 to implement various functions of the image processing apparatus 12.

The display control unit 60 transmits a signal indicating the information to be displayed by a display device 24 to the display device 24. An example of the information to be displayed by the display device 24 is a classification map indicating the segmented medical image.

The classification map can be applied to the input medical image to generate the segmentation mask. The segmentation mask storage unit 84 may store the classification map as the result of the segmentation.

The input control unit 62 converts a signal indicating input information transmitted from the input device 21 into a signal in a format applied to the image processing apparatus 12. The signal indicating the input information is appropriately transmitted to each unit of the apparatus.

[Hardware Configuration of Image Processing Unit]

<Overall Configuration>

Figure 3:
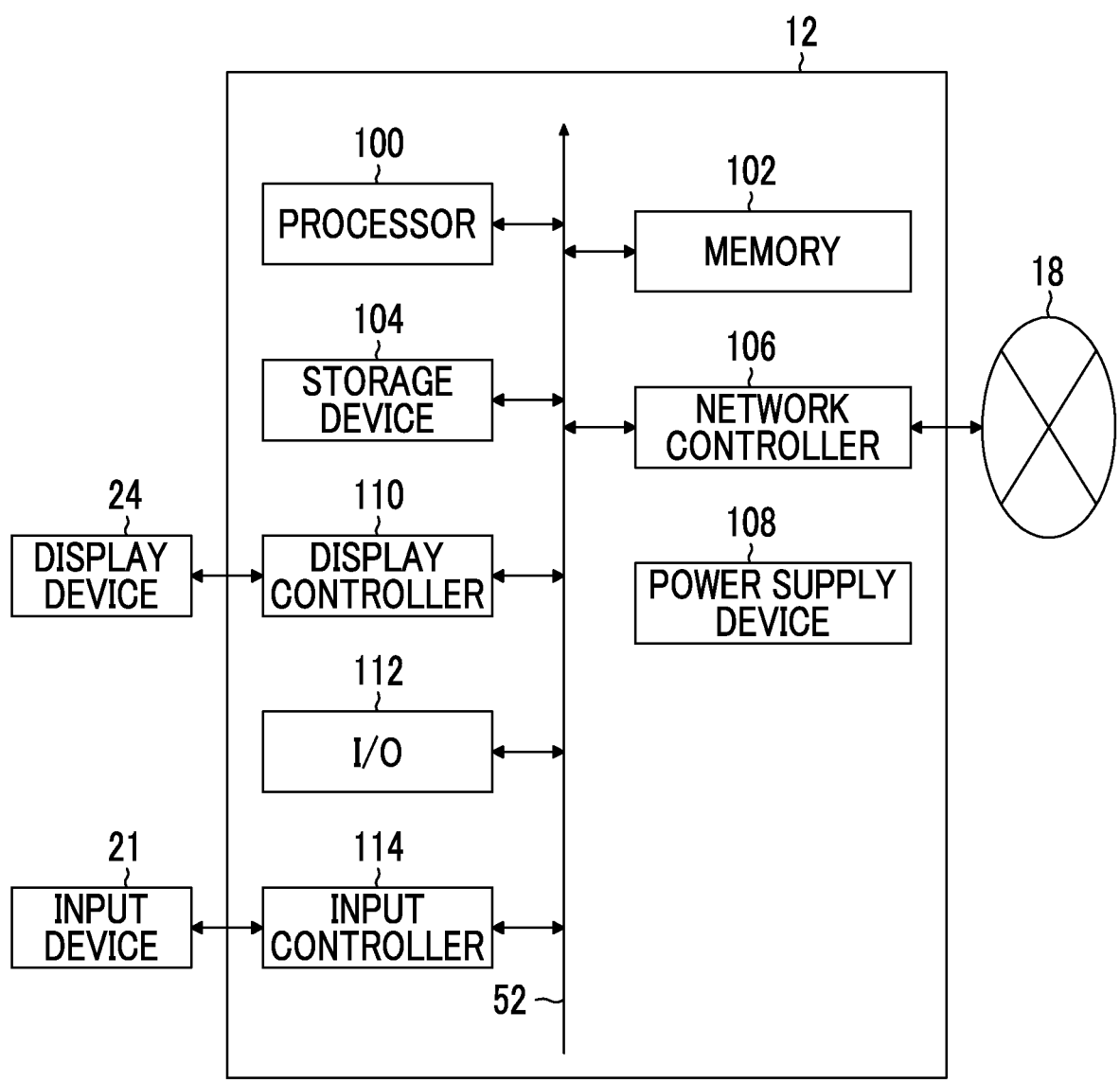
FIG. 3 is a block diagram illustrating a hardware configuration of the image processing apparatus illustrated in FIG. 1.

FIG. 3 is a block diagram illustrating the hardware configuration of the image processing apparatus illustrated in FIG. 1. The image processing apparatus 12 can execute a prescribed program using the hardware illustrated in FIG. 3 to implement various functions.

The image processing apparatus 12 comprises a processor 100, a memory 102, a storage device 104, a network controller 106, and a power supply device 108. Further, the image processing apparatus 12 comprises a display controller 110, an input/output interface 112, and an input controller 114.

The processor 100, the memory 102, the storage device 104, the network controller 106, the display controller 110, the input/output interface 112, and the input controller 114 are connected through the bus 52 so as to perform data communication therebetween.

<Processor>

The processor 100 functions as an overall control unit for the image processing apparatus 12, various arithmetic units, and a storage control unit. The processor 100 executes programs stored in a read only memory (ROM) provided in the memory 102.

The processor 100 may execute a program downloaded from an external storage device through the network controller 106. The external storage device may be connected so as to communicate with the image processing apparatus 12 through the network 18.

The processor 100 performs various processes in cooperation with various programs, using a random access memory (RAM) provided in the memory 102 as an arithmetic region. In this way, various functions of the image processing apparatus 12 are implemented.

The processor 100 controls the reading of data from the storage device 104 and the writing of data to the storage device 104. The processor 100 may acquire various types of data from the external storage device through the network controller 106. The processor 100 can execute various processes, such as calculations, using the acquired various types of data.

The processor 100 may include one device or two or more devices. Examples of the processor 100 include a field programmable gate array (FPGA) and a programmable logic device (PLD). The FPGA and the PLD are devices whose circuit configurations can be changed after manufacture.

Another example of the processor 100 is an application specific integrated circuit (ASIC). The ASIC has a dedicated circuit configuration that is designed in order to perform a specific process.

Two or more devices of the same type can be applied as the processor 100. For example, two or more FPGAs or two or more PLDs may be used as the processor 100. Two or more devices of different types may be applied as the processor 100. For example, one or more FPGAs and one or more ASICs may be applied as the processor 100.

In a case in which a plurality of processors 100 are provided, the plurality of processors 100 may be configured by one device. As an example in which the plurality of processors 100 are configured by one device, there is an aspect in which a combination of one or more central processing units (CPUs) and software is used to configure one processor and the processor functions as the plurality of processors 100. In addition, the software in the specification is synonymous with a program.

A graphics processing unit (GPU) which is a device specialized for image processing may be applied instead of the CPU or in addition to the CPU. A computer is given as a representative example in which a plurality of processors 100 are configured by one device.

As another example in which the plurality of processors 100 are configured by one device, there is an aspect in which a device that implements all of the functions of a system including the plurality of processors 100 with one IC chip is used. A system on chip (SoC) is given as a representative example of the device that implements all of the functions of the system including the plurality of processors 100 with one IC chip. In addition, IC is an abbreviation of Integrated Circuit.

As such, the hardware structure of the processor 100 is configured by one or more various devices.

<Memory>

The memory 102 comprises a ROM (not illustrated) and a RAM (not illustrated). The ROM stores various programs executed by the image processing apparatus 12. The ROM stores, for example, files and parameters used to execute various programs. The RAM functions as, for example, a temporary data storage region and a work area of the processor 100.

<Storage Device>

The storage device 104 non-temporarily stores various types of data. The storage device 104 may be attached to the outside of the image processing apparatus 12. A high-capacity semiconductor memory device may be applied instead of or in addition to the storage device 104.

<Network Controller>

The network controller 106 controls data communication with an external apparatus. The control of the data communication may include the management of data communication traffic. A known network, such as a local area network (LAN), may be applied as the network 18 connected through the network controller 106.

<Power Supply Device>

A high-capacity power supply device, such as an uninterruptible power supply (UPS), is applied as the power supply device 108. The power supply device 108 supplies power to the image processing apparatus 12 in a case in which a commercial power supply is cut off due to, for example, a power failure.

<Display Controller>

The display controller 110 functions as a display driver that controls the display device 24 on the basis of a command signal transmitted from the processor 100.

<Input/Output Interface>

The input/output interface 112 connects the image processing apparatus 12 and an external apparatus so as to communicate with each other. A communication standard, such as a universal serial bus (USB), may be applied as the input/output interface 112.

<Input Controller>

The input controller 114 converts the format of the signal input by the input device 21 into a format suitable for the processing of the image processing apparatus 12. The information input from the input device 21 through the input controller 114 is transmitted to each unit through the processor 100.

In addition, the hardware configuration of the image processing apparatus 12 illustrated in FIG. 3 is an illustrative example, and some components of the hardware configuration can be appropriately added, removed, and changed.

Detailed Description of Segmentation According to First Embodiment

Next, the segmentation of a medical image according to a first embodiment will be described. For example, segmentation that extracts one or more lesions from a CT image of the lung is a very difficult operation even for a skilled observer. On the other hand, in a case in which global information, such as a disease name and a respiratory state at the time of imaging, is used, it is possible to exclude the existence of a specific lesion from the segmentation mask using the association between the global information and the lesion.

Therefore, a discrimination apparatus that has performed learning, using a learning set which is a combination of local information to which a lesion is applied and global information to which a disease name is applied, is applied to segment a medical image with good robustness.

Figure 4:
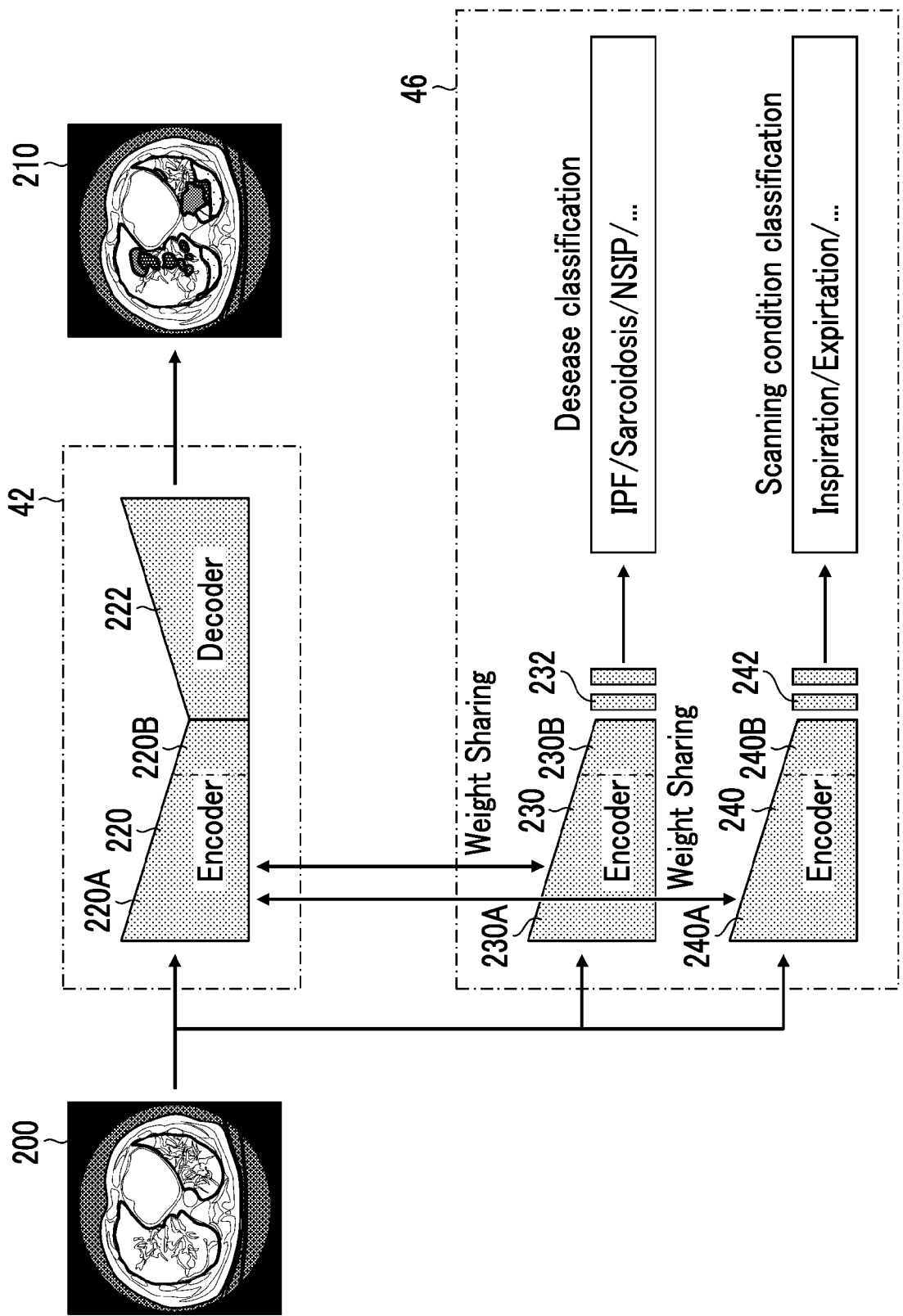
FIG. 4 is a diagram schematically illustrating a neural network applied to an image processing apparatus according to a first embodiment.

FIG. 4 is a diagram schematically illustrating a neural network applied to the image processing apparatus according to the first embodiment. The segmentation network 42 performs segmentation on a CT image 200 of the lung which is a medical image to generate the segmentation mask 210. Further, in the following description, the CT image 200 of the lung will be referred to as a CT image 200.

The segmentation network 42 comprises a first encoder unit 220 and a decoder unit 222. The CT image 200 is set as an input image of the first encoder unit 220 through the image acquisition unit 40 illustrated in FIG. 2.

The CT image 200 set as the input of the segmentation network 42 is set as the input of the decoder unit 222 through the processing of a first low-order layer 220A and a first high-order layer 220B. The first low-order layer 220A of the first encoder unit 220 in the segmentation network 42 shares weights with a second low-order layer 230A of a second encoder unit 230 and a third low-order layer 240A of a third encoder unit 240 in the classification network 46. In addition, the weight may be called a parameter, a coefficient, and the like.

That is, the first low-order layer 220A of the first encoder unit 220 and the second low-order layer 230A of the second encoder unit 230 apply the same weight to process the CT image 200. In other words, the first low-order layer 220A of the first encoder unit 220 and the second low-order layer 230A of the second encoder unit 230 perform the same processing on the CT image 200 and generate the same processing result. This holds for the first low-order layer 220A of the first encoder unit 220 and the third low-order layer 240A of the third encoder unit 240.

The first encoder unit 220 and the decoder unit 222 are configured by combining a convolution filter and an activation unit. The first encoder unit 220 generates a low-resolution feature amount map from the CT image 200. That is, the first high-order layer 220B of the first encoder unit 220 performs a process specialized for segmentation on the processing result of the first low-order layer 220A to generate a feature amount map.

The decoder unit 222 converts the feature amount map generated by the first encoder unit 220 so as to have the same size as the CT image 200. A probability map indicating the probability of a lesion existing in each pixel may be applied as the segmentation mask 210 output from the segmentation network 42.

Figure 5:
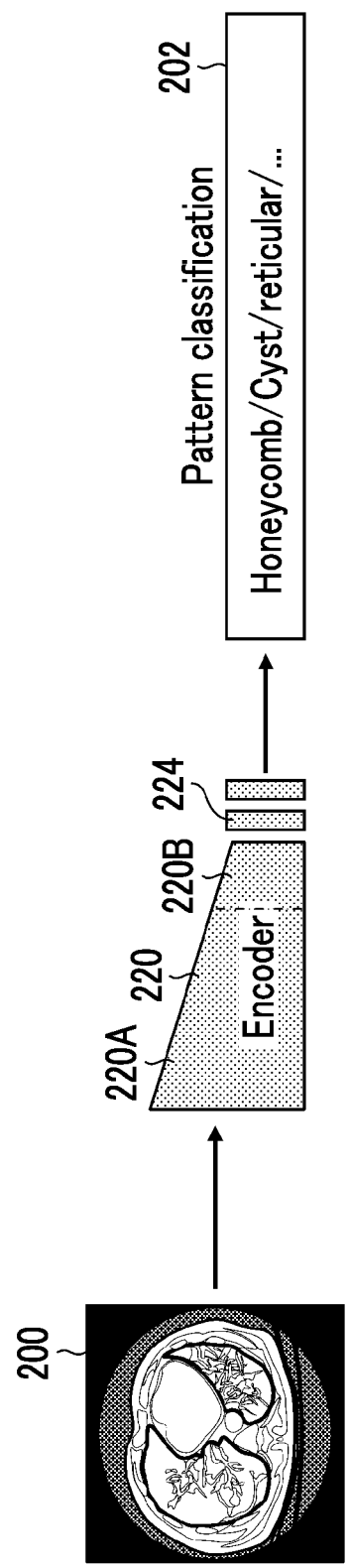
FIG. 5 is a diagram schematically illustrating an example of a first encoder unit illustrated in FIG. 4.

FIG. 5 is a diagram schematically illustrating an example of the first encoder unit illustrated in FIG. 4. An output unit 224 of the first encoder unit 220 illustrated in FIG. 5 outputs the feature amount map indicating the lesion in the CT image 200.

FIG. 5 illustrates lesion information 202 in which the lesions in the CT image 200 applied to the feature amount map is listed. The decoder unit 222 illustrated in FIG. 4 outputs the segmentation mask 210 obtained by converting the feature amount map so as to have the same size as the CT image 200.

Here, the concept of "same" is not limited to "exactly the same". For example, sizes in different processing ranges can be included in the same size. As the concept of "same" and "equal" in the specification, the above-mentioned concept is applied unless otherwise described.

The classification network 46 illustrated in FIG. 4 includes a plurality of neural networks. A neural network comprising the second encoder unit 230 and a neural network comprising the third encoder unit 240 are given as an example of the plurality of neural networks. The classification network 46 may comprise three or more encoders to which different global features are applied or may comprise one encoder.

The classification network 46 outputs the global feature indicating the overall feature of the medical image. A disease name is applied as the global feature to the second encoder unit 230. That is, the second high-order layer 230B of the second encoder unit 230 performs a process specialized for the classification applied to the second encoder unit 230 on the processing result of the second low-order layer 230A to extract the disease name of the CT image 200. A second output layer 232 outputs the disease name of the CT image 200.

FIG. 4 illustrates idiopathic pulmonary fibrosis, sarcoidosis, and nonspecific interstitial pneumonia as examples of the disease names. In addition, IPF illustrated in FIG. 4 is an abbreviation of Idiopathic Pulmonary Fibrosis. NSIP is an abbreviation of Nonspecific Interstitial Pneumonia.

Respiratory conditions at the time of the capture of the CT image 200 are applied as the global feature to the third encoder unit 240. The third high-order layer 240B of the third encoder unit 240 performs a process specialized for the classification applied to the third encoder unit 240 on the processing result of the third low-order layer 240A to extract the respiratory conditions at the time of the capture of the CT image 200. A third output layer 242 outputs the respiratory conditions at the time of the capture of the CT image 200.

FIG. 4 illustrates expiration and inspiration as the respiratory conditions at the time of the capture of the CT image 200.

The second encoder unit 230 and the third encoder unit 240 are configured by a combination of a convolution filter and an activation unit similarly to the first encoder unit 220. While the output of the segmentation network 42 is a probability map, the output of the classification network 46 is a probability vector indicating the existence probability of the global feature corresponding to the entire CT image 200.

That is, the second output layer 232 of the second encoder unit 230 outputs the existence probability of the disease name corresponding to the entire CT image 200. Further, the third output layer 242 of the third encoder unit 240 outputs the existence probability of the respiratory conditions at the time of imaging which corresponds to the entire CT image 200.

The classification network 46 applies a fully connected layer to convert a low-resolution feature amount map into a one-dimensional feature vector, without using the decoder unit 222 of the segmentation network 42.

The error of the segmentation applied to the learning of the segmentation network 42 is calculated from the comparison between the segmentation mask 210 output from the segmentation network 42 and the correct answer data of the segmentation.

The error of the classification applied to the learning of the classification network 46 is calculated from the comparison between the global feature which is the result of the classification and the correct answer data of the classification.

The total error of the segmentation network 42 and the classification network 46 is calculated using the error of each of the segmentation network 42 and the classification network 46.

The weights of the segmentation network 42 and the weights of the classification network 46 are updated by applying backpropagation. As such, the image processing apparatus 12 can collectively learn the local feature indicating the feature of each pixel and the global feature indicating the overall feature of the medical image.

For example, the layer that shares weights with the classification network 46 during the relearning of the segmentation network 42 can use the result of the segmentation, the result of the classification, and the CT image 200 as a learning set.

On the other hand, the segmentation network 42 and the classification network 46 may individually perform relearning such that the weights of the low-order layer of the segmentation network 42 and the weights of the low-order layer of the classification network 46 are shared.

The layer that does not share weights with the classification network 46 during the relearning of the segmentation network 42 may use the result of the segmentation and the CT image 200 as a learning set.

The segmentation network 42 that has performed relearning is an example of a deep learning device that has performed relearning using the segmentation result of the segmentation unit, the classification result of the global feature classification unit, and the input medical image as a learning set.

The same configuration can be applied to the second encoder unit 230 and the third encoder unit 240 applied to the classification network 46. In addition, different configurations may be applied to the second encoder unit 230 and the third encoder unit 240. [Application Examples to Convolutional Neural Network]

Figure 6:
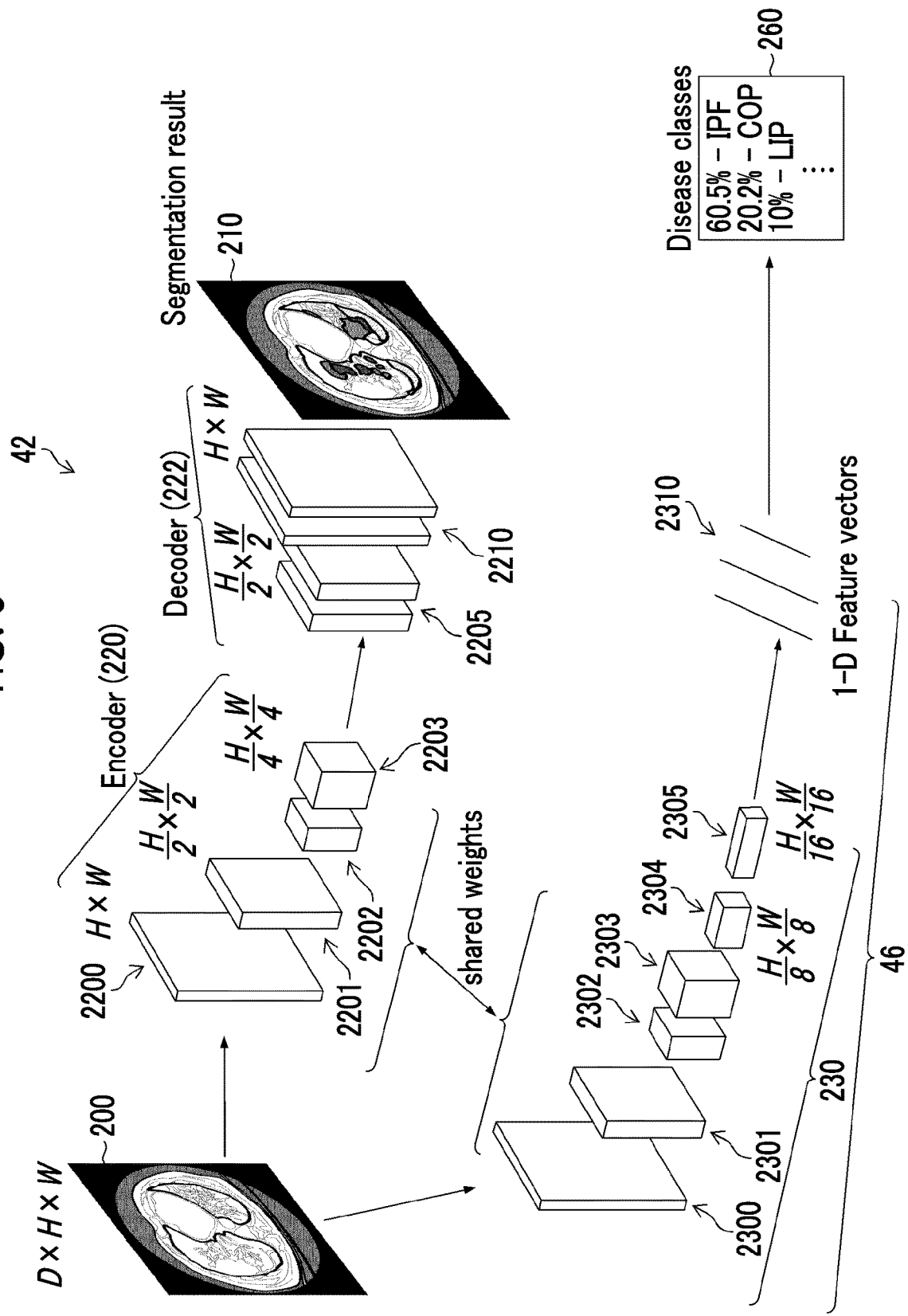
FIG. 6 is a diagram schematically illustrating a convolutional neural network applied to the image processing apparatus according to the first embodiment.

FIG. 6 is a diagram schematically illustrating a convolutional neural network applied to the image processing apparatus according to the first embodiment. In some cases, the convolutional neural network is expressed as a CNN using an abbreviation of Convolutional Neural Network. In addition, for simplification of description, the third encoder unit 240 of the classification network 46 illustrated in FIG. 5 is not illustrated in FIG. 6.

Letter D indicates the axial number of the CT image 200. For simplification of FIG. 6, the illustration of the axial number D is omitted in a portion that schematically illustrates the processing of the CT image 200. This holds for FIG. 8.

Letter H indicates the size of the CT image 200 in the vertical direction. Letter W indicates the size of the CT image 200 in the horizontal direction. H×W indicates the size of the CT image 200. The number of pixels can be applied as the size of the CT image 200. For example, H may be the number of pixels in the vertical direction, and W may be the number of pixels in the horizontal direction.

The first encoder unit 220 of the segmentation network 42 comprises an input layer 2200, a first interlayer 2201, a second interlayer 2202, and a third interlayer 2203. The first interlayer 2201, the second interlayer 2202, and the third interlayer 2203 may be generically referred to as interlayers. The interlayers may be configured by repeating a convolution layer and a pooling layer.

The first interlayer 2201 convolves the CT image 200 acquired through the input layer 2200. The first interlayer 2201 generates an image having a size of (H/2)×(W/2).

Similarly, the second interlayer 2202 convolves the image output from the first interlayer 2201 to generate an image having a size of (H/4)×(W/4).

Further, the third interlayer 2203 convolves the image output from the second interlayer 2202 to generate an image having a size of (H/8)×(W/8). The first interlayer 2201, the second interlayer 2202, and the third interlayer 2203 illustrated in FIG. 6 correspond to the first low-order layer 220A illustrated in FIG. 4. In addition, the first high-order layer 220B illustrated in FIG. 4 is not illustrated in FIG. 6.

The decoder unit 222 comprises a fifth interlayer 2205 and an output layer 2210. The decoder unit 222 comprises a fourth interlayer (not illustrated) provided in a stage before the fifth interlayer 2205, which is not illustrated.

The decoder unit 222 converts the output image of the first encoder unit 220 so as to have the same size as the CT image 200. For example, the fifth interlayer 2205 converts the image having a size of (H/2)×(W/2) into an image having a size of H×W.

The second encoder unit 230 of the classification network 46 comprises an input layer 2300, a first interlayer 2301, a second interlayer 2302, a third interlayer 2303, a fourth interlayer 2304, a fifth interlayer 2305, and an output layer 2310.

The first interlayer 2301, the second interlayer 2302, and the third interlayer 2303 correspond to the second low-order layer 230A and the third low-order layer 240A illustrated in FIG. 4. The fourth interlayer 2304 and the fifth interlayer 2305 correspond to the second high-order layer 230B and the third high-order layer 240B illustrated in FIG. 4. Further, the output layer 2310 of the classification network 46 illustrated in FIG. 6 corresponds to the second output layer 232 illustrated in FIG. 4.

the first to third interlayers 2301 to 2303 of the second encoder unit 230 apply the same sequence as the first to third interlayers 2201 to 2203 of the first encoder unit 220 to perform convolution. On the other hand, the fourth interlayer 2304 and the fifth interlayer 2305 of the second encoder unit 230 apply a sequence specialized for the classification applied to the second encoder unit 230 to perform convolution.

A fully connected layer is applied as the output layer 2310, and the output layer 2310 outputs a one-dimensional feature vector indicating the global feature of the CT image 200. The output layer 2310 illustrated in FIG. 6 outputs a probability vector 260 indicating the likelihood of the global feature of the CT image 200. The probability vector 260 illustrated in FIG. 6 shows that the probability of IPF is 60.5%, the probability of cryptogenic organizing pneumonia (COP) is 20.2%, and the probability of lymphocyite interstitial pneumonia (LIP) is 10%.

As illustrated in FIG. 6, the first interlayer 2201 of the segmentation network 42 shares weights with the first interlayer 2301 of the classification network 46. Further, the second interlayer 2202 of the segmentation network 42 shares weights with the second interlayer 2302 of the classification network 46.

Further, the third interlayer 2203 of the segmentation network 42 shares weights with the third interlayer 2303 of the classification network 46. That is, the low-order layer of the segmentation network 42 shares weights with the low-order layer of the classification network 46.

That is, at least some of the interlayers of the segmentation network 42 share weights with the corresponding interlayers of the classification network 46. For example, the interlayer of the segmentation network 42 may share weights with the interlayer of the classification network 46 that performs the same convolution.

The interlayers closer to the input layer pay attention to the same feature in a case in which a lesion is extracted from CT image 200 and in a case in which a disease name is extracted from CT image 200. Therefore, the low-order layer which is an interlayer closer to the input layer in the segmentation network 42 shares weights with the low-order layer of the classification network 46. As a result, in the segmentation of the CT image 200, information applied to the extraction of the global feature of the CT image 200 can be used, and the robustness of the segmentation of the CT image 200 can be improved.

The low-order layers in each network can be defined by applying, for example, experiments and simulations. That is, one or more layers that shares weights in a case in which good results are obtained while the layers sharing weights are appropriately changed can be defined as the low-order layers.

Further, in a case in which the relearning of the segmentation network 42 is performed, local information and global information are learned together. Therefore, the segmentation network 42 can ensure higher robustness.

Operation and Effect of Image Processing Apparatus According to First Embodiment According to the image processing apparatus 12 according to the first embodiment having the above-mentioned configuration, it is possible to obtain the following operation and effect.

[1]

The first encoder unit 220 of the segmentation network 42 shares weights with at least one of the second encoder unit 230 or the third encoder unit 240 of the classification network 46. Therefore, the segmentation network 42 can use the medical image feature extraction applied to the classification network 46 and can improve the robustness of the segmentation.

[2]

In a case in which the relearning of the segmentation network 42 is performed, the segmentation network 42 learns the local information applied to the segmentation network 42 and the global information applied to the classification network 46 together. Therefore, the segmentation network 42 can ensure higher robustness.

[3]

The low-order layer of the segmentation network 42 shares weights with the low-order layer of the classification network 46. Therefore, the low-order layer of the segmentation network 42 can use the features of the medical image extracted in the low-order layer of the classification network 46.

Image Processing Apparatus According to Second Embodiment

Detailed Description of Segmentation According to Second Embodiment

Figure 7:
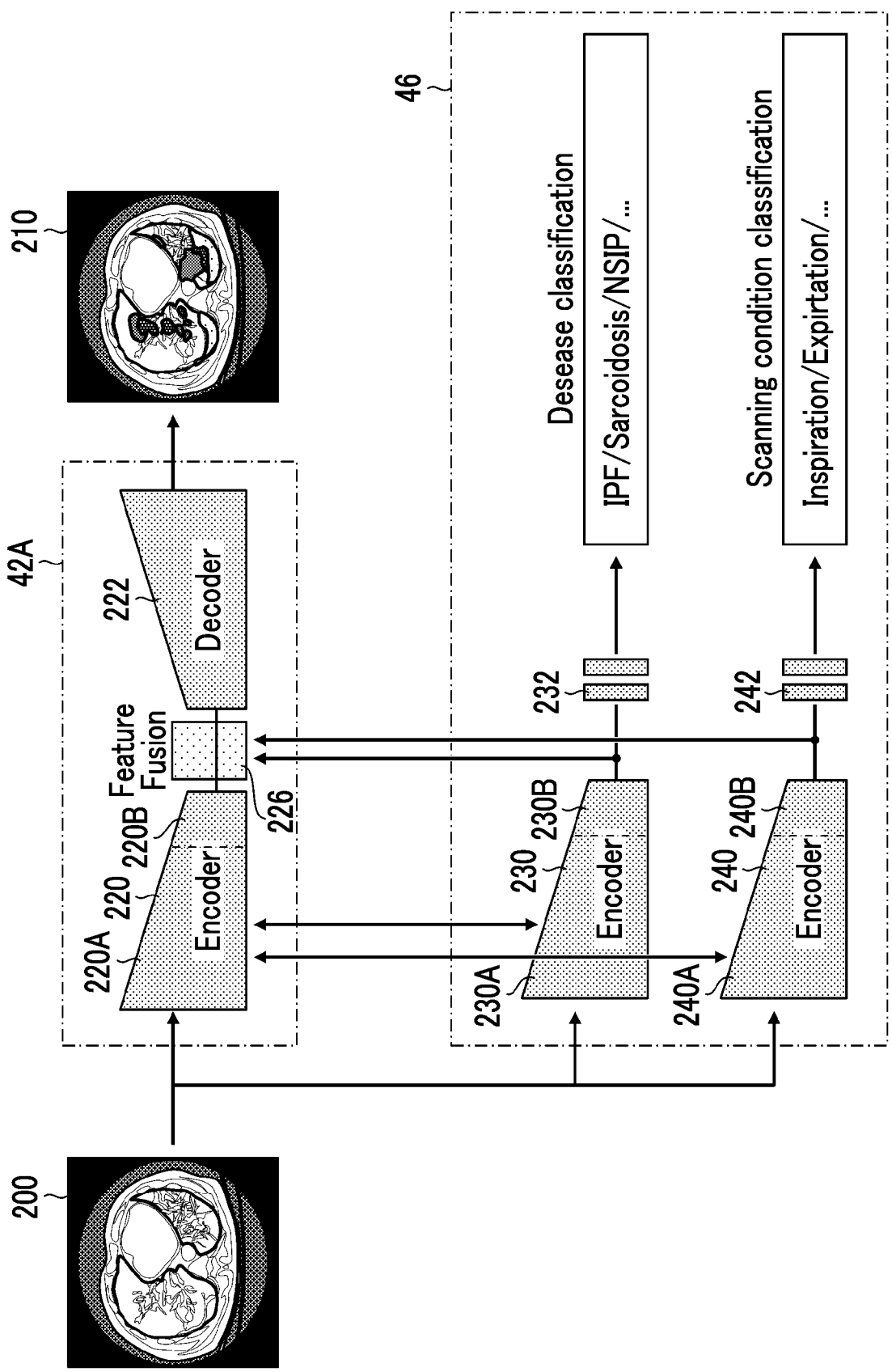
FIG. 7 is a diagram schematically illustrating a neural network applied to an image processing apparatus according to a second embodiment.

FIG. 7 is a diagram schematically illustrating a neural network applied to an image processing apparatus according to a second embodiment. A segmentation network 42A illustrated in FIG. 7 comprises a combination unit 226 between the first encoder unit 220 and the decoder unit 222.

The combination unit 226 combines an output image of the first encoder unit 220 and an output image of the second encoder unit 230. Further, the combination unit 226 combines the output image of the first encoder unit 220 and an output image of the third encoder unit 240.

The combination unit 226 transmits the output image to the decoder unit 222. The decoder unit 222 converts the size of the input image to generate a segmentation mask 210 having the same size as the CT image 200.

An error of segmentation, an error of classification, and the total error of segmentation and classification are calculated in the same manner as those in the image processing apparatus 12 according to the first embodiment.

The weights of the segmentation network 42A and the weights of the classification network 46 are updated by applying backpropagation. Similarly to the image processing apparatus 12 according to the first embodiment, the image processing apparatus according to the second embodiment can collectively learn the local feature indicating the feature of each pixel and the global feature indicating the overall feature of the medical image.

Of course, the relearning of the segmentation network 42A and the classification network 46 may be individually performed such that the weights of the low-order layer of the segmentation network 42A and the weights of the low-order layer of the classification network 46 are shared.

Application Examples to Convolutional Neural Network

Figure 8:
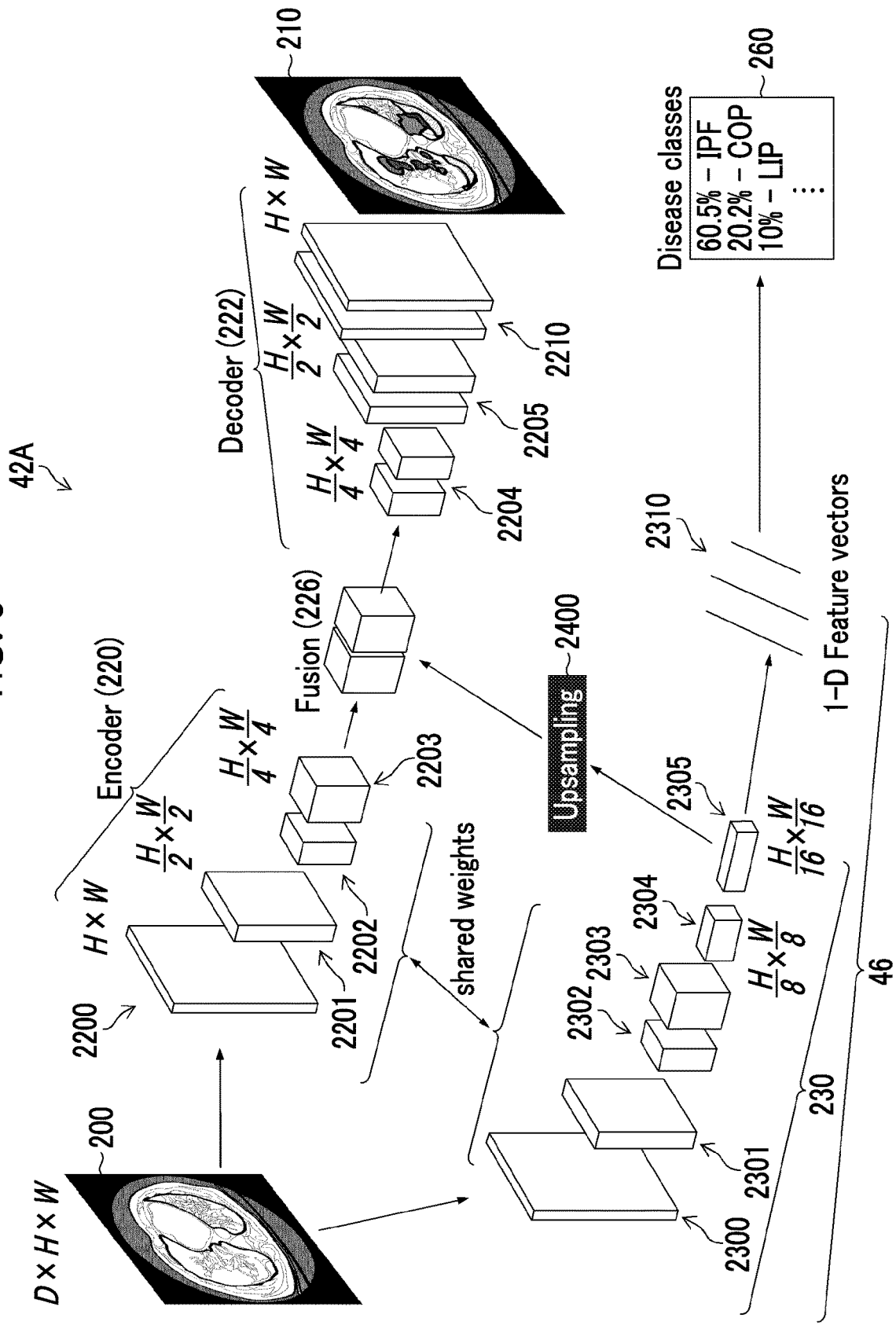
FIG. 8 is a diagram schematically illustrating a convolutional neural network applied to the image processing apparatus according to the second embodiment.

FIG. 8 is a diagram schematically illustrating a convolutional neural network applied to the image processing apparatus according to the second embodiment. An output image of the fifth interlayer 2305 of the second encoder unit 230 is transmitted to an upsampling unit 2400. In addition, the fifth interlayer 2305 is an interlayer in a stage before an output unit that outputs a one-dimensional feature vector and is an example of the interlayer that does not share weights with the first encoder unit.

The upsampling unit 2400 converts the size of the output image of the fifth interlayer 2305 such that the output image of the fifth interlayer 2305 has the same size as the output image of the third interlayer 2203. The upsampling unit 2400 transmits the output image of the fifth interlayer 2305 whose size has been converted to the combination unit 226.

The combination unit 226 combines the output image of the third interlayer 2203 and the output image of the upsampling unit 2400 and transmits the combined image to a fourth interlayer 2204 of the decoder unit 222. The decoder unit 222 converts the size of the output image of the combination unit 226 to generate a segmentation mask 210 having the same size as the CT image 200.

The output image of the high-order layer of the classification network 46 is more compressed than the image applied to the segmentation network 42 and has a smaller size than the image. Therefore, the upsampling unit 2400 enlarges the output image of the classification network 46. The combination unit 226 combines the output image of the high-order layer of the classification network 46 whose size has been converted and the output image of the first encoder unit 220 of the segmentation network 42.

In addition, the upsampling unit 2400 according to the embodiment is an example of a conversion unit that expands the output image of the second encoder unit in accordance with the output image of the first encoder unit.

In this embodiment, the aspect in which the output image of the fifth interlayer 2305 is transmitted to the upsampling unit 2400 has been described. However, the image which is output from the second low-order layer 230A of the second encoder unit 230, such as the fourth interlayer 2304, and is output from a layer in the stage before the output layer 2310 may be transmitted to the upsampling unit 2400.

The amount of information of the output image of, for example, the fifth interlayer 2305 which is a layer in the stage before the output layer 2310 is not less than that of the one-dimensional feature vector output from the output layer 2310. Therefore, the image whose amount of information is kept constant can be combined with the output image of the first encoder unit 220.

The input image of the upsampling unit 2400 can be defined using learning. That is, an interlayer that performs learning, using the output image of each interlayer and the image output from the combination unit 226 as a learning set, and outputs the input image of the upsampling unit 2400 can be defined.

[Operation and Effect of Image Processing Apparatus According to Second Embodiment]

According to the image processing apparatus according to the second embodiment having the above-mentioned configuration, it is possible to obtain the following operation and effect.

[1]

The combination unit 226 that combines the output image of the first encoder unit 220 of the segmentation network 42 and the output image of the second encoder unit 230 of the classification network 46 is provided. Therefore, it is possible to segment the medical image of the segmentation network 42 using the features of the medical image extracted by the classification network 46.

[2]

The upsampling unit 2400 that converts the output image of the second encoder unit 230 to have the same size as the output image of the first encoder unit 220 of the segmentation network 42 is provided. Therefore, it is possible to combine the output image of the first encoder unit 220 and the output image of the second encoder unit 230.

[3]

Upsampling is performed on the output image of the interlayer which is provided in the stage before the output layer 2310 of the second encoder unit 230 and does not share weights with the interlayer of the first encoder unit 220, and the output image is combined with the output image of the first encoder unit 220. Therefore, it possible to perform upsampling on the output image of the interlayer of the second encoder unit 230 whose amount of information is kept constant and to combine the output image with the output image of the first encoder unit 220.

[Correspondence Relationship Between Local Feature and Global Feature]

FIG. 9 is a diagram illustrating an example of a table indicating the correspondence relationship between disease names and lesions. A table 250 illustrated in FIG. 9 can be stored in the image database 16 illustrated in FIG. 1.

There is a close relationship between the disease name which is the global feature of a medical image and the lesion which is the feature of a local region of the medical image. As illustrated in FIG. 9, there are lesions that can exist in each disease name and lesions that are not capable of existing in each disease name.

The segmentation network 42 can be trained with reference to the table 250 illustrated in FIG. 9 to improve the robustness of the segmentation network 42. A case is considered in which a disease name other than IPF is extracted as the global feature of the CT image 200. The segmentation network 42 may be configured such that the honeycomb lung unique to IPF is not extracted as the local feature.

In addition, RA illustrated in FIG. 9 is an abbreviation of Rheumatoid Arthritis. SSc is an abbreviation of Systemic Sclerosis. PSS is an abbreviation of Progressive Systemic Sclerosis.

OP is an abbreviation of Organizing Pneumonia. COP is an abbreviation of Cryptogenic Organizing Pneumonia.

DIP is an abbreviation of Desquamative Interstitial Pneumoniae. CNPA is an abbreviation of Chronic Necrotizing Pulmonary Aspergillosis. IPF is an abbreviation of Idiopathic Pulmonary Fibrosis. UIP is an abbreviation of Usual Interstitial Pneumonia.

Application Examples to Image Processing Method

The image processing apparatus 12 according to the first embodiment and the image processing apparatus according to the second embodiment can be configured as an image processing method including steps corresponding to each unit in, for example, the image processing apparatus 12.

The image processing method that performs segmentation on the CT image 200 may include a medical image acquisition step of acquiring the CT image 200. The image processing method may include a classification step of performing classification on the CT image 200. In the segmentation step of performing the segmentation on the CT image 200, the weights of the first low-order layer are shared with the weights of the second low-order layer in the classification step.

The segmentation step may include a first encoding step of compressing the features of the CT image 200 and extracting the features of each pixel of the CT image 200. The segmentation step may include a decoding step of decompressing the features extracted in the first encoding step to generate a segmentation mask. The classification step may include a second encoding step of compressing the features of the CT image 200 and extracting the overall features of the CT image 200.

The image processing method may include a conversion step of converting the size of an output image of an interlayer in the classification step to the size of an output image of an interlayer in the segmentation step. Further, the image processing method may include a combination step of combining the output image in the conversion step with the output image of the interlayer in the segmentation step. In addition, the classification step according to the embodiment is an example of a global feature classification step.

Application Examples to Program

The image processing apparatus 12 according to the first embodiment and the image processing apparatus according to the second embodiment can be configured as a program that causes a computer to implement functions corresponding to each unit of, for example, the image processing apparatus 12.

Examples of the functions corresponding to each unit include a medical image acquisition function of acquiring the CT image 200 and a classification function of performing classification on the CT image 200. Further, examples of the functions corresponding to each unit include a segmentation function of performing segmentation on the CT image 200 and sharing the weights of the first low-order layer with the weights of the second low-order layer in the classification function.

The segmentation function may comprise a first encoding function of compressing the features of the CT image 200 and extracting the features of each pixel of the CT image 200. The segmentation function may comprise a decoding function of decompressing the features extracted by the first encoding function to generate a segmentation mask.

The classification function may comprise a second encoding function of compressing the features of the CT image 200 and extracting the overall features of the CT image 200. Further, examples of the functions corresponding to each unit include a conversion function of converting the output image of the interlayer of the classification network 46 so as to have the same size as the output image of the interlayer of the segmentation network 42.

In addition, examples of the functions corresponding to each unit include a combination function of combining the image converted by the conversion function with the output image of the interlayer of the segmentation network 42. Further, the classification function according to the embodiment is an example of a global feature classification function.

Application Examples to Other Medical Images

In this embodiment, the CT image of the lung is given as an example of the medical image. However, the medical images of organs other than the lung, such as the brain, the stomach, and the intestines, may be used. Further, the medical image is not limited to a two-dimensional image. The medical image may be a three-dimensional image. In the case of the three-dimensional image, segmentation based on the features of each voxel is performed.

Modification Examples of Global Feature

In this embodiment, the disease name and the respiratory conditions at the time of imaging are given as examples of the global features. However, the global features may be information indicating features related to class segmentation or features affecting class classification. For example, information, such as a physique, age, sex, and a previous illness, related to a subject may be applied as the global features. Information indicating the size of the body, such as height and weight, may be applied as the physique.

Modification Examples of Class

In this embodiment, the lesion is given as an example of the class of the segmentation. However, for example, the features of the image patterns of inflammation, tumor, non-tumor, and the like may be applied as the class. In addition, in a case in which there is a standard classification for each modality that generates medical images, the standard classification for each modality can be applied to the class.

Further, multi-class classification may be applied as the segmentation. In the multi-class classification, a probability indicating the likelihood of each of a plurality of classes is calculated for each pixel.

For Combinations of Embodiment, Modification Examples, and the Like

The components described in the above-mentioned embodiment and the components described in the application examples can be appropriately combined with each other. In addition, some of the components may be replaced.

In the above-described embodiment of the invention, components can be appropriately changed, added, and removed without departing from the scope and spirit of the invention. The invention is not limited to the above-described embodiment and can be changed and modified in various ways by those skilled in the art without departing from the technical idea of the invention.

EXPLANATION OF REFERENCES

10: medical information system
12: image processing apparatus
14: modality
16: image database
18: network
20: mouse
21: input device
22: keyboard
24: display device
40: image acquisition unit
42: segmentation network
42A: segmentation network
46: classification network
50: storage unit
52: bus
60: display control unit
62: input control unit
70: feature amount extraction unit
74: segmentation mask generation unit
80: image storage unit
84: segmentation mask storage unit
86: global feature storage unit
88: program storage unit
100: processor
102: memory
104: storage device
106: network controller
108: power supply device
110: display controller
112: input/output Interface
114: input controller
200: CT image
210: segmentation mask
220: first encoder unit
222: decoder unit
224: output unit
226: combination unit
230: second encoder unit
232: second output layer
240: third encoder unit
242: third output layer
250: table
2200: input layer
2201: first interlayer
2202: second interlayer
2203: third interlayer
2204: fourth interlayer
2205: fifth interlayer
2210: output layer
2300: input layer
2301: first interlayer
2302: second interlayer
2303: third interlayer
2304: fourth interlayer
2305: fifth interlayer
2310: output layer
2400: upsampling unit

What is claimed is:

1. An image processing apparatus comprising
at least one processor configured to:
apply deep learning to perform segmentation which classifies a medical image into a specific class on the basis of a local feature of the medical image to generate a segmentation result, wherein the segmentation result indicates a probability of a lesion existing in each pixel of the medical image;
apply deep learning to perform classification for the medical image into a global feature which is an overall feature of the medical image; and
share a weight of a first low-order layer which is a low-order layer in the segmentation, with a second low-order layer which is a low-order layer in the classification into the global feature, wherein, in performing the segmentation, the at least one processor applies a deep learning which has performed learning for a layer that shares weights with the classification into the global feature, using the segmentation result in the segmentation, a classification result in the classification into the global feature, and the medical image input when performing the segmentation, as a learning set.

2. The image processing apparatus according to claim 1, wherein the at least one processor applies a lesion as the class in the segmentation.

3. The image processing apparatus according to claim 1, wherein the at least one processor applies a disease name as the global feature in the classification into the global feature.

4. The image processing apparatus according to claim 1, wherein the at least one processor applies an imaging condition of the medical image as the global feature in the classification into the global feature.

5. The image processing apparatus according to claim 1, comprising:

a first encoder configured to compress features of the medical image, in performing the segmentation;

a decoder configured to decompress the features of the medical image compressed by the first encoder; and a second encoder configured to compress the features of the medical image, in performing the classification into the global feature, wherein a weight that is applied to the first encoder as the weight of the first low-order layer, is shared with a weight applied to the second encoder.

6. The image processing apparatus according to claim 5, comprising:

a convertor configured to expand an output image of the second encoder, which has been more compressed than an output image of the first encoder, in accordance with the output image of the first encoder; and a coupler configured to combine the output image of the first encoder and an output image of the convertor.

7. The image processing apparatus according to claim 6, wherein the second encoder transmits to the convertor, an output image of an interlayer that is provided in a stage before outputting of a one-dimensional feature vector, and the interlayer does not share weights with the first encoder.

8. The image processing apparatus according to claim 6, wherein the convertor applies a deep learning that has performed learning using an input image of the convertor and an output image of the coupler, as a learning set.

9. The image processing apparatus according to claim 1, wherein, in performing the segmentation, the at least one processor applies a deep learning which has performed relearning for a layer that does not share weights with the classification into the global feature, using the medical image and the segmentation result in the segmentation, as a learning set.

10. The image processing apparatus according to claim 1, wherein, in performing the classification into the global feature, the at least one processor applies a deep learning which has performed learning for a layer that shares weights with the segmentation, using the medical image input when performing the classification into the global feature and a classification result in the classification into the global feature, as a learning set.

11. An image processing method comprising:

applying deep learning to perform segmentation which classifies a medical image into a specific class on the basis of a local feature of the medical image to generate a segmentation result, wherein the segmentation result indicates a probability of a lesion existing in each pixel of the medical image; and applying deep learning to perform classification for the medical image into a global feature which is an overall feature of the medical image, wherein, a weight of a first low-order layer which is a low-order layer in the segmentation is shared with a second low-order layer which is a low-order layer in the classification into the global feature, wherein, in performing the segmentation, a deep learning which has performed learning for a layer that shares weights with the classification into the global feature, using the segmentation result in the segmentation, a classification result in the classification into the global feature, and the medical image input is applied when performing the segmentation, as a learning set.

12. A non-transitory computer readable storage medium storing commands that are read by a computer and cause the computer to implement an image processing function comprising:

a segmentation function of applying deep learning to perform segmentation which classifies a medical image into a specific class on the basis of a local feature of the medical image to generate a segmentation result, wherein the segmentation result indicates a probability of a lesion existing in each pixel of the medical image; and a global feature classification function of applying deep learning to classify the medical image into a global feature which is an overall feature of the medical image, wherein the segmentation function shares a weight of a first low-order layer which is a low-order layer in the segmentation function with a second low-order layer which is a low-order layer in the global feature classification function, wherein, in performing the segmentation, a deep learning which has performed learning for a layer that shares weights with the classification into the global feature, using the segmentation result in the segmentation, a classification result in the classification into the global feature, and the medical image input is applied when performing the segmentation, as a learning set.

* * * * *